United States Patent [19]

Hayashi et al.

[11] 4,195,182
[45] Mar. 25, 1980

[54] TRANS-$\Delta^2$-PROSTAGLANDIN ANALOGUES

[75] Inventors: Masaki Hayashi; Seiji Kori, both of Takatsuki; Takanori Okada, Osaka, all of Japan

[73] Assignee: Ono Pharmaceutical Co. Ltd., Osaka, Japan

[21] Appl. No.: 824,384

[22] Filed: Aug. 12, 1977

[30] Foreign Application Priority Data

Aug. 23, 1976 [GB] United Kingdom ............... 35080/76

[51] Int. Cl.$^2$ ............................................. C07C 177/00
[52] U.S. Cl. ........................................ 180/53; 562/463
[58] Field of Search ........................... 560/53; 562/463

[56] References Cited
PUBLICATIONS

Derment Abstr. 65019y/37 Belgium 852.363 12-03-76.
Derment Abstr. 46992y/27 Belgium 850084 05-01-76.

Primary Examiner—Paul J. Killos
Attorney, Agent, or Firm—Albert H. Graddis

[57] ABSTRACT

This invention relates to prostaglandin analogues of the formula:

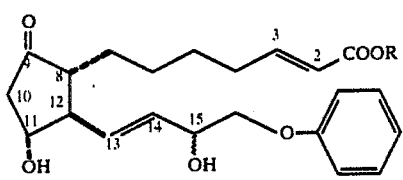

(wherein R represents a hydrogen atom or a methyl group, and the double bonds between $C_2$-$C_3$ and $C_{13}$-$C_{14}$ are trans) and cyclodextrin clathrates of such compounds and, when R represents a hydrogen atom, non-toxic salts thereof, which possess characteristic prostaglandin-like activity.

11 Claims, No Drawings

TRANS-Δ²-PROSTAGLANDIN ANALOGUES

This invention is concerned with new prostaglandin analogues.

Prostaglandins are derivatives of prostanoic acid which has the following formula:

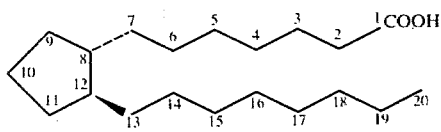

Various types of prostaglandins are known, the types depending inter alia on the structure and substituents on the alicyclic ring. For example, the alicyclic rings of prostaglandins F(PGF) and E(PGE) have the structures:

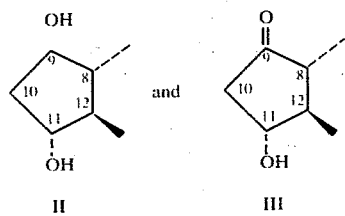

respectively. In the foregoing formulae and in other formulae throughout this specification the dotted lines denote, in accordance with generally accepted rules of nomenclature, that the attached grouping lies behind the general plane of the ring system, i.e. that the grouping is in α-configuration, the thickened lines denote that the grouping lies in front of the general plane of the system, i.e. that the grouping is in β-configuration, and the wavy line indicates that the grouping is in α- or β-configuration.

Such compounds are sub-classified according to the position of double bond(s) in the side chain(s) attached to the 8- and 12-positions of the alicyclic ring. Thus $PG_1$ compounds have a trans-double bond between $C_{13}$–$C_{14}$ (trans-$\Delta^{13}$) and $PG_2$ compounds have a cis-double bond between $C_5$–$C_6$ and a trans-double bond between $C_{13}$–$C_{14}$ (cis-$\Delta^5$, trans-$\Delta^{13}$). For example, prostaglandin $F_{1\alpha}$ ($PGF_{1\alpha}$) and prostaglandin $E_1$ ($PGE_1$) are characterized by the following structures IV and V.

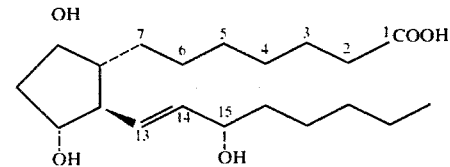

and

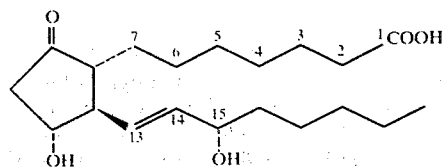

respectively. The structures of $PGF_{2\alpha}$ and $PGE_2$, as members of the $PG_2$ group correspond to those of formulae IV and V respectively, with a cis-double bond between the carbon atoms in positions 5 and 6. Compounds in which the double bond between the carbon atoms in positions 13 and 14 of members of the $PG_1$ group is replaced by ethylene are known as dihydro-prostaglandins, e.g. dihydro-prostaglandin $F_{1\alpha}$ (dihydro-$PGF_{1\alpha}$) and dihydro-prostaglandin $E_1$ (dihydro-$PGE_1$).

Moreover, when one or more methylene groups are added to, or eliminated from, the aliphatic group attached to the 12-position of the alicyclic ring of the prostaglandins the compounds are known, in accordance with the usual rules of organic nomenclature, as homo-prostaglandins (methylene group added) or nor-prostaglandins (methylene group eliminated), and, when more than one methylene group is added or eliminated, the number is indicated by di- tri- etc. before the prefix "homo" or "nor".

Prostaglandins are generally known to possess pharmacological properties, for example they stimulate smooth muscle, have hypotensive, diuretic, bronchodilating and antilipolytic activities, and also inhibit blood platelet aggregation and gastric acid secretion, and are, accordingly, useful in the treatment of hypertension, thrombosis, asthma and gastro-intestinal ulcers, in the induction of labour and abortion in pregnant female mammals, in the prevention of arteriosclerosis, and as diuretic agents. They are fat-soluble substances obtainable in very small quantities from various tissues of animals which secrete the prostaglandins in the living body.

For example, PGEs have an inhibiting effect on gastric acid secretion and may, accordingly, be used in the treatment of gastric ulcers. They also inhibit the release of free fatty acid induced by epinephrine and as a result they reduce the concentration of free fatty acid in blood, and are, accordingly, useful in the prevention of arteriosclerosis and hyperlipemia. $PGE_1$ inhibits blood platelet aggregation and also removes the thrombus and prevents thrombosis. PGEs and PGFs have a stimulating effect on smooth muscle and increase the intestinal peristalsis; these actions indicate therapeutic utility on post-operative ileus and as purgatives. Furthermore, PGEs and PGFs may be used as oxytocics, as abortifacients in the first and second trimesters; in the post-labour abortion of the placenta, and as oral contraceptives because they regulate the sexual cycle of female mammals. PGEs have vasodilator and diuretic activities. PGEs are useful for improvement in patients suffering from cerebral vascular disease because they increase the cerebral blood flow and are also useful in the treatment of asthmatic conditions in patients because of their bronchodilating activity.

During the past decade widespread investigations have been carried out in order to discover inter alia new products possessing the pharmacological properties of the 'natural' prostaglandins or one or more of such properties to an enhanced degree, or hitherto unknown pharmacological properties. It has now been found that by replacing the butyl group attached to the 16-position carbon atom of prostaglandins $E_1$ by a phenoxy group, and by introducing a trans-double bond into the 2-position of the aliphatic group linked to the 8-position of the alicyclic ring, the pharmacological properties of 'natural' prostaglandins are, in some aspects of their activities, improved or modified.

The present invention accordingly provides the new prostaglandin analogues of the formula:

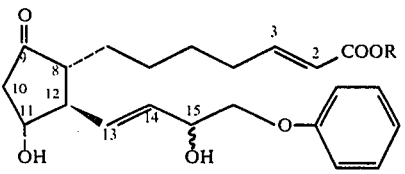

VI (wherein R represents a hydrogen atom or a methyl group, and the double bonds between $C_2$–$C_3$ and $C_{13}$–$C_{14}$ are trans) and cyclodextrin clathrates of such compounds and, when R represents a hydrogen atom, non-toxic (e.g. sodium) salts thereof.

The present invention is concerned with all compounds of general formula VI in the 'natural' form or its enantiomeric form, or mixtures thereof, more particularly the racemic form consisting of equimolecular mixtures of natural and its enantiomeric form.

As will be apparent to those skilled in the art, the compounds depicted in general formula VI have at least four centres of chirality, these four centres of chirality being at the alicyclic ring carbon atoms identified as 8, 11, and 12 and at the $C_{15}$ carbon atom which has attached to it a hydroxy group. The presence of chirality leads, as is well known, to the existence of isomerism. However, the compounds of general formula VI all have such a configuration that the side-chains attached to the ring carbon atoms in the positions identified as 8 and 12 are trans with respect to each other. Accordingly, all isomers of general formula VI, and mixtures thereof, which have those side-chains attached to the ring carbon atoms in positions 8 and 12 in the trans-configuration and have a hydroxy group as depicted in the 15-position in α- or β-configuration are to be considered within the scope of general formula VI. Preferably the 15-position hydroxy group is in α-configuration.

According to a feature of the present invention, the prostaglandin analogues of formula VI, wherein R is as hereinbefore defined, are prepared by the process which comprises hydrolysing a compound of the formula:

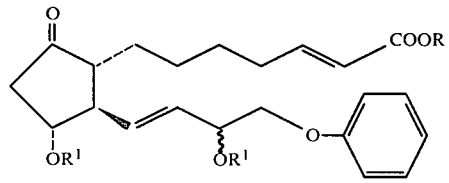

VII (wherein $R^1$ represents a 2-tetrahydrofuranyl or 1-ethoxyethyl group or, preferably, a 2-tetrahydropyranyl group unsubstituted or substituted by at least one alkyl group, and R is as hereinbefore defined) to convert to hydroxy groups the groups $OR^1$ to obtain a PGE compound of formula VI.

The groups $OR^1$ of compounds of formula VII may be converted to hydroxy groups by mild hydrolysis with an aqueous solution of an organic acid, e.g. acetic acid, or with a dilute aqueous inorganic acid, e.g. hydrochloric acid, advantageously in the presence of an organic solvent miscible with water, e.g. tetrahydrofuran or an alkanol containing from 1 to 4 carbon atoms, e.g. methanol. The mild hydrolysis may be carried out at a temperature ranging from ambient to 75° C. (preferably at a temperature below 45° C.) with an acid mixture, e.g. a mixture of hydrochloric acid with tetrahydrofuran or methanol, or a mixture of acetic acid, water and tetrahydrofuran. The products of formula VI may be purified by column chromatography on silica gel, which procedure may, when the starting material of formula VII is a mixture of compounds with the group $OR^1$ in the 15-position in α- and β-configuration, lead to a separation of the resulting 15α- and 15β-hydroxy isomers of formula VI.

Compounds of formula VII may be prepared from a compound of the formula:

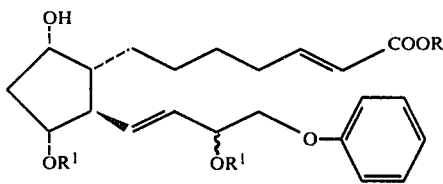

VIII (wherein R and $R^1$ are as hereinbefore defined) by methods known per se for the conversion of a hydroxy group in the 9-position of a prostaglandin compound to an oxo group, for example by means of a chromic acid solution (e.g. obtained from chromium trioxide, manganese sulphate and sulphuric acid in water) or Jones' reagent or Collins' reagent or a dimethyl sulphide-N-chlorosuccinimide complex.

Compounds of formula VIII may be prepared from a compound of the formula:

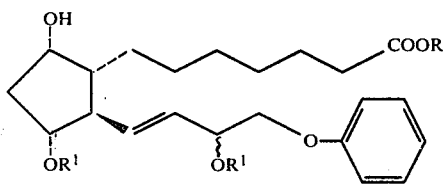

IX (wherein R and $R^1$ are as hereinbefore defined) as follows.

Compounds of formula IX may be converted to compounds of the formula:

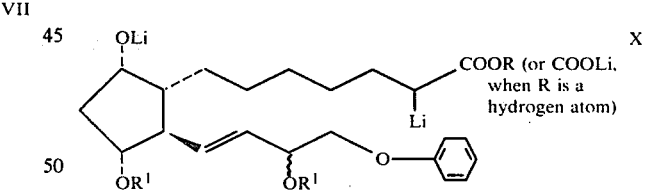

X (wherein R and $R^1$ are as hereinbefore defined) by reaction with a compound of the formula:

XI (wherein $R^2$ and $R^3$ each represent an alkyl group containing from 1 to 6 carbon atoms or a cycloalkyl group containing from 3 to 6 carbon atoms), e.g. lithium diisopropylamide, (1) when R represents a methyl group, in tetrahydrofuran at a low temperature, e.g. at −78° C., or (2) when R represents a hydrogen atom, in tetrahydrofuran in the presence of hexamethylphosphotriamide at 0° C.

Compounds of formula X may be converted to compounds of the formula:

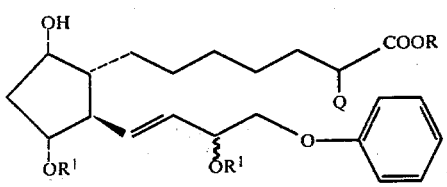

XII (wherein Q represents the group —SeC$_6$H$_5$ or —SR$^4$, in which R$^4$ represents an alkyl group containing from 1 to 4 carbon atoms or a phenyl group, and R and R$^1$ are as hereinbefore defined) by reaction with benzeneselenenyl bromide (i.e. C$_6$H$_5$SeBr) or diphenyldiselenide (i.e. C$_6$H$_5$SeSeC$_6$H$_5$) or a dialkyldisulphide or diphenyldisulphide of the formula R$^4$SSR$^4$, in which R$^4$ is as hereinbefore defined, in an inert organic solvent, e.g. tetrahydrofuran, hexamethylphosphotriamide, diethyl ether, n-hexane, or n-pentane, or a mixture of two or more of them, at a low temperature, when R is a methyl group, e.g. −78° C., or, when R is a hydrogen atom, at 0° C., followed by hydrolysis of the resulting organolithium compound, for example by treatment with an aqueous solution of ammonium chloride, to give compounds of formula XII.

Compounds of formula XII, wherein Q represents the group —SeC$_6$H$_5$, may be converted to compounds of formula VIII by reaction (1) with hydrogen peroxide in a mixture of ethyl acetate and tetrahydrofuran or methanol, preferably in the presence of sodium bicarbonate, at a temperature below 30° C., or (2) with sodium periodate in a mixture of water and a lower alkanol, e.g. methanol or ethanol, preferably in the presence of sodium bicarbonate, at a temperature below 30° C.

Compounds of formula XII, wherein Q represents the group —SR$^4$ (R$^4$ being as hereinbefore defined), may be converted to compounds of the formula:

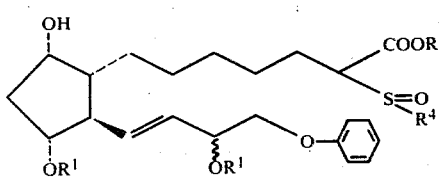

XIII (wherein the various symbols are as hereinbefore defined) by means heretofore mentioned for the conversion of compounds of formula XII, wherein Q represents the group —SeC$_6$H$_5$, to those of formula VIII.

Compounds of formula XIII may be converted to compounds of formula VIII by treatment (1) when R$^4$ represents an alkyl group, in toluene, preferably in the presence of a small amount of calcium carbonate, at a temperature of 100° to 120° C., or (2) when R$^4$ represents a phenyl group, in carbon tetrachloride, preferably in the presence of a small amount of calcium carbonate, at a temperature of about 50° C.

Compounds of formula IX may be prepared from a compound of the formula:

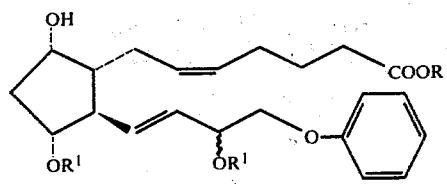

XIV (wherein R and R$^1$ are as hereinbefore defined) by reduction. Suitably, the reduction may be effected by hydrogenation in the presence of a hydrogenation catalyst, e.g. palladium on carbon or palladium black, in the presence of an inert organic solvent, for example a lower alkanol, e.g. methanol or ethanol, at laboratory temperature at normal or elevated pressure, e.g. at a hydrogen pressure from atmospheric to 15 kg/cm$^2$.

Compounds of formula XIV may be prepared from a compound of the formula:

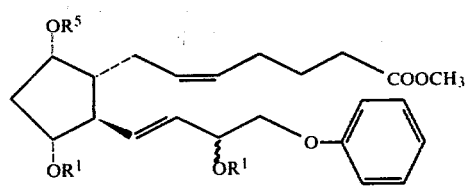

XV (wherein R$^5$ represents an alkylcarbonyl group containing from 2 to 5 carbon atoms, and R$^1$ is as hereinbefore defined) by hydrolysis under alkaline conditions. The hydrolysis under alkaline conditions may be effected (1) with an aqueous solution of an alkali metal, e.g. sodium or potassium, hydroxide or carbonate in the presence of a water-miscible solvent, e.g. tetrahydrofuran or methanol, to give a compound of formula XIV, wherein R represents a hydrogen atom, or (2) with anhydrous potassium carbonate in anhydrous methanol, to give a compound of formula XIV, wherein R represents a methyl group.

Compounds of formula XV may be prepared from a compound of the formula:

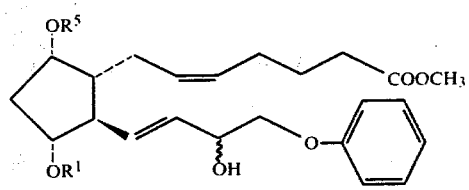

XVI (wherein R$^1$ and R$^5$ are as hereinbefore defined) by reaction with a dihydropyran, dihydrofuran or ethyl vinyl ether in an inert organic solvent, e.g. methylene chloride, in the presence of a condensing agent, e.g. p-toluenesulphonic acid.

Compounds of formula XVI may be prepared from a compound of the formula:

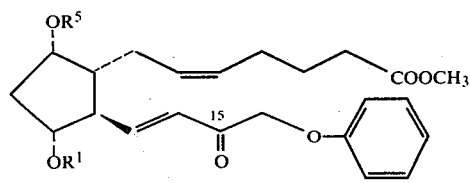

XVII

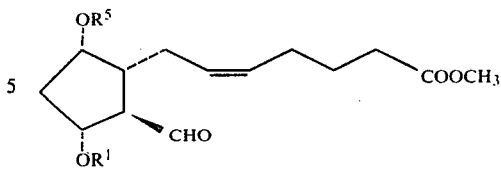

XVIII (wherein R$^1$ and R$^5$ are as hereinbefore defined) by reduction to convert the 15-oxo group to a hydroxy group. The reduction is suitably effected (1) with excess sodium borohydride in an alkanol containing from 1 to 4 carbon atoms, e.g., methanol, at a low temperature, preferably at −30° to −60° C., or (2) with zinc borohydride in a suitable inert organic solvent, e.g. 1,2-dimethoxyethane, at −10° to 10° C. The product thus obtained is a mixture of isomers in which the hydroxy group at position 15 is in α- or β-configuration. If desired, the isomer having the hydroxy group in α-configuration may be separated from the isomer having the hydroxy group in β-configuration by column chromatography on silica gel.

Compounds of formula XVII may be prepared by the Wittig reaction of a compound of the formula:

(wherein the various symbols are as hereinbefore defined) with the sodium derivative of a dialkyl phosphonate of the formula:

$$(R^6O)_2-\underset{\underset{O}{\|}}{P}CH_2\underset{\underset{O}{\|}}{C}CH_2O-\phantom{xx}\text{XIX}$$

wherein R$^6$ represents an alkyl group containing from 1 to 4 carbon atoms. The reaction is preferably effected by suspending sodium hydride in an inert organic solvent, e.g. tetrahydrofuran or 1,2-dimethoxyethane, and adding the dialkyl phosphonate of formula XIX. The resulting sodium derivative of the dialkyl phosphonate may be reacted with compounds of formula XVIII at 20° to 45° C. to form the transenone compound of formula XVII stereoselectively.

The method hereinbefore described for the preparation of compounds of formula VI may be represented by the series of reactions depicted schematically in Scheme A, wherein the various symbols are as hereinbefore defined.

SCHEME A

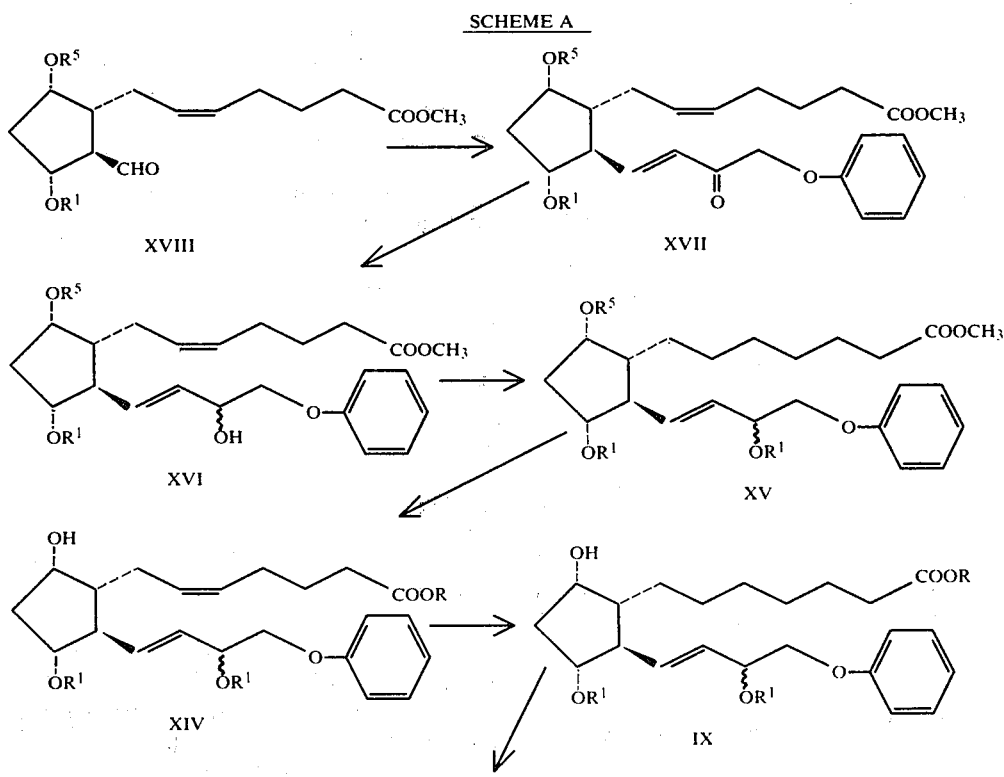

-continued
SCHEME A

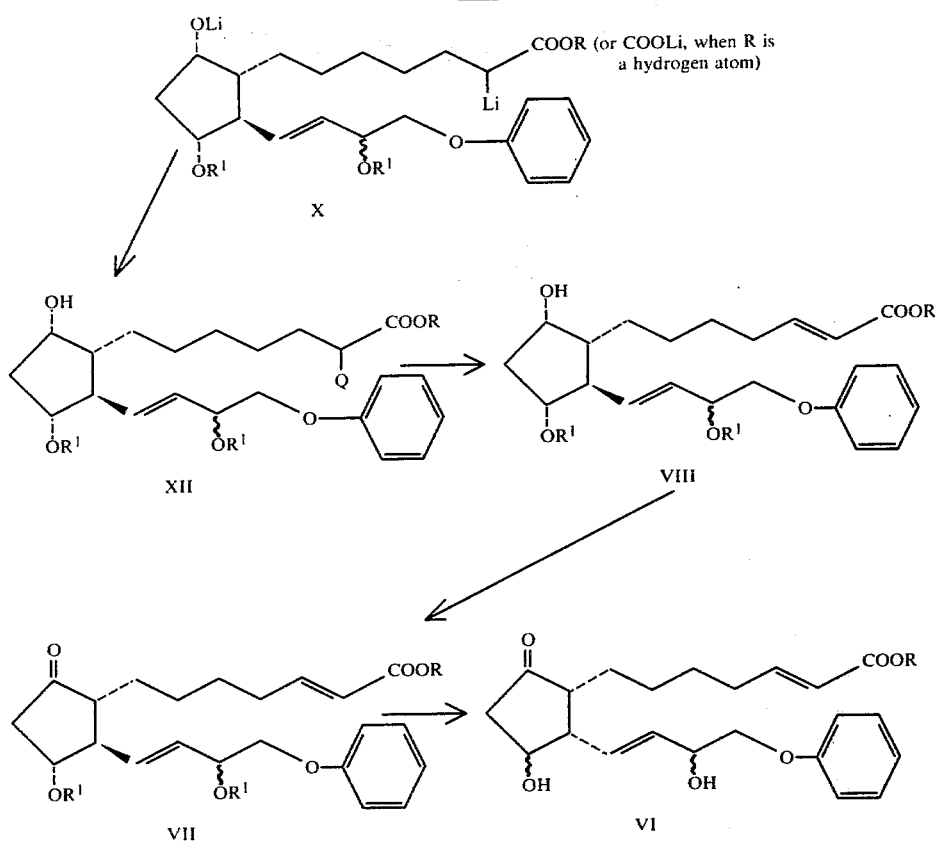

In formulae VI to X and XII to XVIII depicted heretofore the double bonds in the $C_2$–$C_3$, $C_5$–$C_6$ and $C_{13}$–$C_{14}$ positions are trans, cis and trans respectively.

Compounds of formula XVIII, wherein $R^1$ and $R^5$ are as hereinbefore defined, used as starting materials in the hereinbefore described procedure, may be prepared by the methods described in Japanese Patent Publication No. 50-82034 and Belgian Pat. Specification No. 834915 from the known compound of the formula:

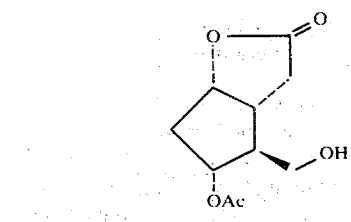

XX wherein Ac represents the acetyl group [described in J. Amer. Chem. Soc., 91, 5675 (1969) and ibid., 92, 397, (1970) by E. J. Corey et al].

Compounds of formula XIX, wherein $R^6$ represents an alkyl group, e.g. methyl, may be prepared as described in British Pat. No. 1464471, U.S. Pat. No. 3,953,435 and Belgium Pat. No. 824196.

Compounds of formula VIII may also be prepared from the known compound of formula XXI [prepared as described in Japanese Pat. Publication No. 49-102646] by the series of reactions depicted schematically below in Scheme B, wherein the various symbols are as hereinbefore defined.

SCHEME B

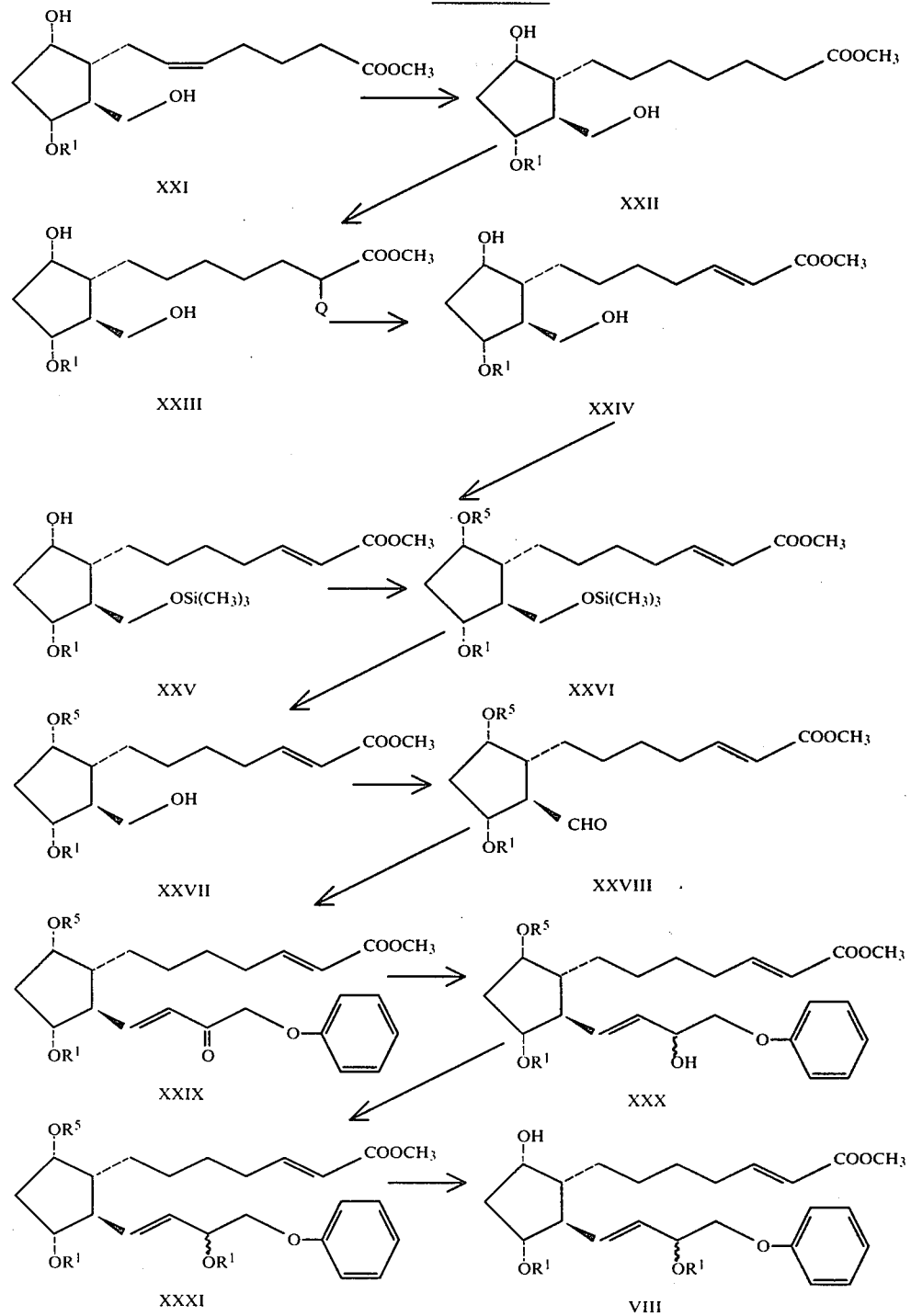

In these formulae the double bonds in the $C_2$-$C_3$ and $C_{13}$-$C_{14}$ positions are trans and the double bond at $C_5$-$C_6$ is cis.

The series of reactions XXI→XXIV (via XXII and XXIII) depicted in Scheme B may be effected as hereinbefore described for the series of reactions XIV→VIII (via IX and XII) in Scheme A.

Compounds of formula XXV may be prepared by reacting compounds of formula XXIV with trimethylchlorosilane in an inert organic solvent, e.g. methylene chloride, in the presence of a base, e.g. pyridine or a tertiary amine, at a low temperature, e.g. at −30° to 0° C.

Compounds of formula XXVI may be prepared by reacting a trimethylsilyl ether of formula XXV with an appropriate acyl chloride or acid anhydride in an inert organic solvent, e.g. methylene chloride, in the presence of a base, e.g. pyridine or a tertiary amine, at a low temperature, e.g. at 0° to 30° C.

Compounds of formula XXVII may be prepared by treating compounds of formula XXVI by methods known per se for the removal of the trimethylsilyl group, for example by treatment with an acid: it is preferable not to use a strong acid in order to avoid the risk of the removal of the group $R^1$.

Compounds of formula XXVII may be converted to compounds of formula XXVIII under mild and neutral conditions, for example with chromium trioxide-pyridine complex or Jones' reagent at a moderately low temperature.

The series of reactions XXVIII→VIII (via XXIX, XXX and XXXI) depicted in Scheme B may be effected as hereinbefore described for the series of reactions XVIII→XIV (via XVII, XVI and XV) in Scheme A.

The methyl ester of a trans-$\Delta^2$-prostaglandin of formula VI (i.e. a compound of that formula wherein R represents a methyl group) may be obtained by methylation by methods known per se of the corresponding acid of formula VI, wherein R represents a hydrogen atom, with, for example, (i) diazomethane, (ii) methanol in the presence of dicyclohexylcarbodiimide as a condensing agent, or (iii) methanol following the formation of a mixed acid anhydride by adding a tertiary amine and then a pivaloyl halide or an arylsulphonyl or alkylsulphonyl halide (cf. British Pat. Nos. 1362956 and 1364125).

Acids of formula VI, wherein R represents a hydrogen atom, may, if desired, be converted by methods known per se into non-toxic salts.

By the term "non-toxic salts", as used in this specification, is meant salts the cations of which are relatively innocuous to the animal organism when used in therapeutic doses so that the beneficial pharmacological properties of the compounds of formula VI are not vitiated by side-effects ascribable to those cations. Preferably the salts are water-soluble. Suitable salts include the alkali metal, e.g. sodium and potassium, and ammonium salts and pharmaceutically acceptable (i.e. non-toxic) amine salts. Amines suitable for forming such salts with carboxylic acids are well known and include, for example, amines derived in theory by the replacement of one or more of the hydrogen atoms of ammonia by groups, which may be the same or different when more than one hydrogen atom is replaced, selected from, for example, alkyl groups containing from 1 to 6 carbon atoms and hydroxyalkyl groups containing from 1 to 3 carbon atoms.

The non-toxic salts may be prepared from acids of formula VI wherein R represents a hydrogen atom by, for example, reaction of stoichiometric quantities of an acid of formula VI and the appropriate base, e.g. an alkali metal hydroxide or carbonate, ammonium hydroxide, ammonia or an amine, in a suitable solvent. The salts may be isolated by lyophilisation of the solution, or, if sufficiently insoluble in the reaction medium, by filtration, if necessary after removal of part of the solvent.

Cyclodextrin clathrates of the prostaglandin analogues of formula VI may be prepared by dissolving the cyclodextrin in water or an organic solvent which is miscible with water and adding to the solution the prostaglandin analogue in a water-miscible organic solvent. The mixture is then heated and the desired cyclodextrin clathrate product isolated by concentrating the mixture under reduced pressure or by cooling and separating the product by filtration or decantation. The ratio of organic solvent to water may be varied according to the solubilities of the starting materials and products. Preferably the temperature is not allowed to exceed 70° C. during the preparation of the cyclodextrin clathrates. $\alpha$-, $\beta$- or $\gamma$-Cyclodextrins or mixtures thereof may be used in the preparation of the cyclodextrin clathrates. Conversion into their cyclodextrin clathrates serves to increase the stability of the prostaglandin analogues.

The prostaglandin analogues of formula VI and their cyclodextrin clathrates and, when R represents a hydrogen atom, non-toxic salts thereof, and more especially 16-phenoxy-17,18,19,20-tetranor-trans-$\Delta^2$-PGE$_1$ methyl ester and its cyclodextrin clathrates, possess the valuable pharmacological properties typical of the prostaglandins in a selective fashion, in particular inhibitory activity on gastric acid secretion and gastric ulceration, stimulatory activity on uterine contraction and abortifacient, luteolytic and antinidatory activity, and are useful in the treatment of gastric ulceration, in the termination of pregnancy and induction of labour in pregnant female mammals and in the treatment of impaired fertility, the control of oestrus, contraception and menstrual regulation in female mammals. For example, in standard laboratory tests with the aforesaid methyl ester, (i) in stress ulceration of the rat [produced according to the method of Takagi and Okabe—Jap. J. Pharmac., 18, 9–18 (1968) by soaking rats in a water bath at 19° C. for 6 hours], it produces 60.8% and 75.4% inhibitions of stress ulceration by oral administration at the doses of 20 and 50 $\mu$g/kg animal body weight, respectively, (ii) it produces an increase in gastric acid pH from 2.0–2.5 to at least 4.0 in 50% of pentagastrin-treated rats when perfused into the stomach at the rate of 0.044 $\mu$g/animal/minute, (iii) in inhibition of gastric acid secretion of fistula dogs when the compound was administered via an oral probe 30 minutes prior to the subcutaneous injection of tetragastrin (4 $\mu$g/kg), it produces 79.2% and 74.6% inhibition of acid output at the doses of 5.0 and 2.5 $\mu$g/kg animal body weight, respectively, (iv) in indomethacin ulceration of the rat [Indomethacin 20 mg/kg animal body weight was administered orally to Wistar male rats weighing 170–200 g after starvation for 24 hours. A single dose of the compound was administered by means of an oral probe 10 minutes prior to the indomethacin administration. The number and the size of the ulcers were determined 6 hours after the indomethacin administration], it produces 70.6%, 71.5% and 91.7% inhibition of indomethacin ulceration at the doses of 0.5, 1 and 5 $\mu$g/kg animal body weight, respectively, (v) it stimulates uterine contraction in the pregnant female rat when administered intravenously on the 20th day of gestation at the dose of 0.2 $\mu$g/kg animal body weight, and (vi) it produces an abortifacient effect in pregnant female rats when administered intraperitoneally on the 17th day of pregnancy at the dose of 0.2 $\mu$g/kg animal body weight or on the 17th and 18th days of pregnancy at the daily dose of 0.05 $\mu$g/kg animal body weight.

16-Phenoxy-17,18,19,20-tetranor-trans-$\Delta^2$-PGE$_1$ methyl ester and its cyclodextrin clathrates possess relatively low potencies in inducing diarrhoea in comparison with their potencies in respect of the valuable properties hereinbefore described; for example the dose by oral administration of the ester required to produce diarrhoea in 50% of mice so treated is 0.63 mg/kg animal body weight.

The compounds of general formula VII and VIII are new compounds and as such constitute further features of the invention.

The following Reference Examples and Examples illustrate the preparation of new prostaglandin analogues of the present invention. In them 'IR', 'NMR' and 'TLC' represent respectively 'Infrared absorption spectrum', 'Nuclear magnetic resonance spectrum' and 'Thin layer chromatography'. Where solvent ratios are specified in chromatographic separations, the ratios are by volume.

REFERENCE EXAMPLE 1

Methyl
9α-acetoxy-11α,15α-bis(2-tetrahydropyranyloxy)-16-phenoxy-17,18,19,20-tetranorprosta-cis-5,trans-13-dienoate To a solution of 1.454 g of methyl 9α-acetoxy-11α-(2-tetrahydropyranyloxy)-15α-hydroxy-16-phenoxy-17,18,19,20-tetranorprosta-cis-5,trans-13-dienoate (prepared as described in British Pat. No. 1464471, U.S. Pat. No. 3953435 and Belgium Pat. No. 824196) in 50 ml of methylene chloride were added a catalytic amount of p-toluenesulphonic acid and 0.61 ml of 2,3-dihydropyran, and the mixture was stirred at room temperature for 20 minutes. The reaction mixture was then diluted with ethyl acetate, washed with aqueous solutions of sodium bicarbonate and of sodium chloride, dried over magnesium sulphate and concentrated under reduced pressure. The residue was purified by column chromatography on silica gel using a mixture of benzene and ethyl acetate (1:4) as eluent to give 1.613 g of the title compound having the following physical characteristic: TLC (developing solvent, benzene-ethyl acetate=2:1): Rf=0.71.

REFERENCE EXAMPLE 2

Methyl
9α-hydroxy-11α,15α-bis(2-tetrahydropyranyloxy)-16-phenoxy-17,18,19,20-tetranorprosta-cis-5,trans-13-dienoate To a solution of 1.613 g of methyl 9α-acetoxy-11α,15α-bis(2-tetrahydropyranyloxy)-16-phenoxy-17,18,19,20-tetranorprosta-cis-5,trans-13-dienoate (prepared as described in Reference Example 1) in 24 ml of methanol were added 380 mg of potassium carbonate, and the mixture was stirred at 40° C. for 2 hours. The reaction mixture was quenched with 1 N hydrochloric acid, diluted with ethyl acetate, washed with aqueous solutions of sodium bicarbonate and of sodium chloride, dried over magnesium sulphate and concentrated under reduced pressure. The residue was purified by column chromatography on silica gel using a mixture of cyclohexane and ethyl acetate (1:1) as eluent to give 1.329 g of the title compound having the following physical characteristics:
TLC (developing solvent, benzene-ethyl acetate=2:1): Rf=0.58;
NMR (CDCl$_3$ solution): δ; 7.5-6.7 (5H, m), 6.0-5.2 (4H, m), 5.0-4.3 (2H, m), 4.3-3.2 (12H, m).

REFERENCE EXAMPLE 3

Methyl
9α-hydroxy-11α,15α-bis(2-tetrahydropyranyloxy)-16-phenoxy-17,18,19,20-tetranorprost-trans-13-enoate 1.27 g of methyl 9α-hydroxy-11α,15α-bis(2-tetrahydropyranyloxy)-16-phenoxy-17,18,19,20-tetranorprostacis-5,trans-13-dienoate (prepared as described in Reference Example 2) were hydrogenated at a pressure of one atmosphere in 30 ml of methanol containing 310 mg of 5% palladium on carbon. The reduction was stopped after the absorption of one equivalent of hydrogen gas. The catalyst was filtered off, and the filtrate was concentrated under reduced pressure. The residue was purified by column chromatography on silica gel using a mixture of benzene and ethyl acetate (1:1) as eluent to give 1.089 g of the title compound having the following physical characteristics:
TLC (developing solvent, benzene-ethyl acetate=2:1): Rf=0.49;
IR (liquid film): ν; 3450, 2950, 2850, 1736, 1598, 975, 815, 755 cm$^{-1}$;
NMR (CDCl$_3$ solution): δ; 7.6-6.7 (5H, m), 5.9-5.3 (2H, m), 5.0-4.4 (3H, m), 4.4-3.2 (12H, m).

REFERENCE EXAMPLE 4

Methyl
2-phenylseleno-9α-hydroxy-11α,15α-bis(2-tetrahydropyranyloxy)-16-phenoxy-17,18,19,20-tetranorprost-trans-13-enoate Under an atmosphere of nitrogen, 3.81 ml of a 1.5 M solution of n-butyllithium in n-hexane were added dropwise to a solution of 0.81 ml of diisopropylamine in 15 ml of tetrahydrofuran at −78° C., and the mixture was stirred at that temperature for 15 minutes to give a lithium diisopropylamide solution. To the lithium diisopropylamide solution was added dropwise over 20 minutes a solution of 1.089 g of methyl 9α-hydroxy-11α,1-5α-bis(2-tetrahydropyranyloxy)-16-phenoxy-17,18,19,20-tetranorprost-trans-13-enoate (prepared as described in Reference Example 3) in 10 ml of tetrahydrofuran at −78° C., and the mixture was stirred at that temperature for 30 minutes. To the solution thus obtained was added dropwise a solution of 1.84 g of diphenyldiselenide in 15 ml of tetrahydrofuran, and the mixture was stirred at −78° C. for one hour. The reaction mixture was quenched with a saturated aqueous solution of ammonium chloride, diluted with ethyl acetate, washed with 1 N hydrochloric acid, an aqueous solution of sodium bicarbonate, water and an aqueous solution of sodium chloride, dried over magnesium sulphate and concentrated under reduced pressure. The residue was purified by column chromatography on silica gel using a mixture of benzene and ethyl acetate (4:1) as eluent to give 895 mg of the title compound having the following physical characteristics:
TLC (developing solvent, benzene-ethyl acetate=2:1): Rf=0.49;
IR (liquid film): ν; 3500, 2950, 2850, 1730, 1600, 980, 875, 820, 740 cm$^{-1}$;
NMR (CDCl$_3$ solution): δ; 7.9-6.7 (10H, m), 5.9-5.3 (2H, m), 5.0-4.4 (3H, m), 4.4-3.1 (12H, m).

EXAMPLE 1

Methyl
9α-hydroxy-11α,15α-bis(2-tetrahydropyranyloxy)-16-phenoxy-17,18,19,20-tetranorprosta-trans-2,trans-13-dienoate To a solution of 895 mg of methyl 2-phenylseleno-9α-hydroxy-11α,15α-bis(2-tetrahydropyranyloxy)-16-phenoxy-17,18,19,20-tetranorprost-trans-13-enoate (prepared as described in Reference Example 4) in 15 ml of a mixture of ethyl acetate and tetrahydrofuran (1:2) were added 0.67 ml of 30% hydrogen peroxide, and the mixture was stirred at 40° to 50° C. for one hour. The reaction mixture was then diluted with 50 ml of water, and extracted with ethyl acetate. The extract was washed with an aqueous solution of sodium bicarbonate, water and an aqueous solution of sodium chloride, dried over magnesium sulphate and concentrated under reduced pressure to give 704 mg of the crude title compound having the following physical characteristics:

TLC (developing solvent, benzene-ethyl acetate=2:1): Rf=0.34;

IR (liquid film): $\nu$; 3450, 2950, 2870, 1720, 1650, 1600, 980, 875, 820, 760 cm$^{-1}$;

NMR (CDCl$_3$ solution): $\delta$; 7.5–6.6 (6H, m), 6.1–5.4 (3H, m), 5.0–3.2 (15H, m).

EXAMPLE 2

Methyl 9-oxo-11$\alpha$,15$\alpha$-bis(2-tetrahydropyranyloxy)-16-phenoxy-17,18,19,20-tetranorprosta-trans-2,trans-13-dienoate A chromic acid solution (obtained from 3.3 g of manganese sulphate, 0.774 ml of conc. sulphuric acid and 0.652 g of chromium trioxide in 16.7 ml of water) was added to a solution of 500 mg of methyl 9$\alpha$-hydroxy-11$\alpha$,15$\alpha$-bis(2-tetrahydropyranyloxy)-16-phenoxy-17,18,19,20-tetranorprostatrans-2,trans-13-dienoate (prepared as described in Example 1) in 80 ml of diethyl ether at 0° to 5° C., and the mixture was stirred at that temperature for 1.5 hours. The reaction mixture was then extracted with diethyl ether, the extract washed with water and an aqueous solution of sodium chloride, dried over magnesium sulphate and concentrated under reduced pressure to give 430 mg of the crude title compound having the following physical characteristics:

TLC (developing solvent, benzene-ethyl acetate=2:1): Rf=0.64;

IR (liquid film): $\nu$; 2950, 2875, 1750, 1730, 1660, 1605, 980, 880, 820, 760 cm$^{-1}$;

NMR (CDCl$_3$ solution): $\delta$; 7.6–6.6 (6H, m), 6.2–5.6 (3H, m), 5.1–3.2 (13H, m).

EXAMPLE 3

Methyl 9-oxo-11$\alpha$,15$\alpha$-dihydroxy-16-phenoxy-17,18,19,20-tetranorprosta-trans-2,trans-13-dienoate [or 16-phenoxy-17,18,19,20-tetranor-trans-$\Delta^2$-PGE$_1$ methyl ester]

A solution of 430 mg of methyl 9-oxo-11$\alpha$,15$\alpha$-bis(2-tetrahydropyranyloxy)-16-phenoxy-17,18,19,20-tetranorprosta-trans-2,trans-13-dienoate (prepared as described in Example 2) in a mixture of 8.6 ml of tetrahydrofuran and 36 ml of 65% aqueous acetic acid was stirred at 60° to 65° C. for 20 minutes, and the reaction mixture was then poured into ice-water. The solution was extracted with ethyl acetate. The extract was washed with water and an aqueous solution of sodium chloride, dried over magnesium sulphate and concentrated under reduced pressure. The residue was purified by column chromatography on silica gel using a mixture of cyclohexane and ethyl acetate (1:1) as eluent to give 225 mg of the title compound having the following physical characteristics:

TLC (developing solvent, chloroform-tetrahydrofuran-acetic acid=10:2:1): Rf=0.42;

IR (liquid film): $\nu$; 3400, 2950, 2860, 1745, 1725, 1655, 1600, 1590, 1500, 1440, 1250, 1080, 1040, 980, 760 cm$^{-1}$;

NMR (CDCl$_3$ solution): $\delta$; 7.40–6.60 (6H, m), 5.90–5.50 (3H, m), 4.52 (1H, broad s), 4.70–3.80 (3H, m), 3.69 (3H, s), 2.73 (1H, dd).

EXAMPLE 4

$\beta$-Cyclodextrin clathrate of methyl 9-oxo-11$\alpha$,15$\alpha$-dihydroxy-16-phenoxy-17,18,19,20-tetranorprosta-trans-2,trans-13-dienoate A solution of 3.2 mg of methyl 9-oxo-11$\alpha$,15$\alpha$-dihydroxy-16-phenoxy-17,18,19,20-tetranorprosta-trans-2,trans-13-dienoate (prepared as described in Example 3) in 0.2 ml of ethanol was added to a solution of 43 mg of $\beta$-cyclodextrin in 0.5 ml of water, and the mixture was stirred at room temperature for 5 minutes. The mixture was concentrated under reduced pressure to give 41.7 mg of the $\beta$-cyclodextrin clathrate of the compound specified in the title. The content of prostaglandin analogue in the product was 7.7%.

The present invention includes within its scope pharmaceutical compositions which comprise at least one new therapeutically useful compound of general formula VI, or cyclodextrin clathrate or non-toxic salt thereof, together with a pharmaceutical carrier or coating. In clinical practice the new compounds of the present invention will normally be administered orally, vaginally, rectally or parenterally.

Solid compositions for oral administration include compressed tablets, pills, dispersible powders, and granules. In such solid compositions one or more of the active compounds is, or are, admixed with at least one inert diluent such as calcium carbonate, potato starch, alginic acid, mannitol or lactose. The compositions may also comprise, as is normal practice, additional substances other than inert diluents, e.g. lubricating agents, such as magnesium stearate. Liquid compositions for oral administration include pharmaceutically-acceptable emulsions, solutions, suspensions, syrups and elixirs containing inert diluents commonly used in the art, such as water and liquid paraffin. Besides inert diluents such compositions may also comprise adjuvants, such as wetting and suspending agents, and sweetening, flavouring, perfuming and preserving agents. The compositions according to the invention, for oral administration, also include capsules of absorbable material such as gelatin containing one or more of the active substances with or without the addition of diluents or excipients.

Solid compositions for vaginal administration include pessaries formulated in manner known per se and containing one or more of the active compounds.

Solid compositions for rectal administration include suppositories formulated in manner known per se and containing one or more of the active compounds.

Preparations according to the invention for parenteral administration include sterile aqueous or non-aqueous solutions, suspensions, or emulsions. Examples of non-aqueous solvents or suspending media are propylene glycol, polyethylene glycol, vegetable oils such as olive oil, and injectable organic esters such as ethyl oleate. These compositions may also include adjuvants such as preserving, wetting, emulsifying and dispersing agents. They may be sterilised, for example, by filtration through a bacteria-retaining filter, by incorporation of sterilising agents in the compositions or by irradiation. They may also be manufactured in the form of sterile solid compositions, which can be dissolved in sterile water or some other sterile injectable medium immediately before use.

The percentage of active ingredient in the compositions of the invention may be varied, it being necessary that it should constitute a proportion such that a suitable dosage for the therapeutic effect desired shall be obtained. Obviously several unit dosage forms may be administered at about the same time. In general, the preparations should normally contain at least 0.025% by weight of active substance when required for administration by injection; for oral administration the preparations will normally contain at least 0.1% by weight of active substance. The dose employed depends upon the desired therapeutic effect, the route of administration and the duration of the treatment.

In the human adult, the doses per person are generally between 20 and 500 μg by oral administration in the treatment of gastric ulceration and between 0.05 and 500 μg by oral, intravaginal, intrauterine, intravenous, intramuscular and extraovular administration in the termination of pregancy and induction of labour in pregnant females, and in the treatment of impaired fertility, in the control of oestrus, contraception and menstrual regulation in females. In domestic female mammals, such as cows, mares, sows, ewes and bitches, the doses are generally between 0.01 and 50 mg/animal by intramuscular, subcutaneous, intrauterine, intravaginal and intravenous administration for the synchronisation of oestrus, treatment of impaired fertility and in the termination of pregnancy and induction of labour.

The following Example illustrates pharmaceutical compositions according to the invention.

EXAMPLE 5

Methyl 9-oxo-11α,15α-dihydroxy-16-phenoxy-17,18,19,20-tetranorprosta-trans-2,trans-13-dienoate (2 mg) (prepared as described in Example 3) was dissolved in ethanol (10 ml), mixed with mannitol (18.5 g), sieved through a 30-mesh sieve, dried at 30° C. for 90 minutes and again sieved through a 30-mesh sieve. Aerosil (microfine silica, 200 mg) was added and the powder obtained was machine filled into one hundred No. 2 hard gelatin capsules to give capsules each containing 20 μg of methyl 9-oxo-11α,15α-dihydroxy-16-phenoxy-17,18,19,20-tetranorprosta-trans-2,trans-13-dienoate which after swallowing of the capsule is released into the stomach.

We claim:

1. A compound of the formula:

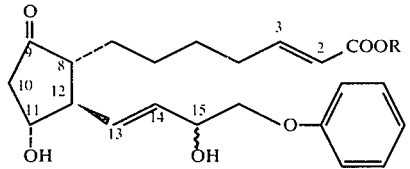

VI (wherein R represents a hydrogen atom or a methyl group, and the double bonds between $C_2$–$C_3$ and $C_{13}$–$C_{14}$ are trans) and cyclodextrin clathrates of such compounds and, when R represents a hydrogen atom, non-toxic salts thereof.

2. A compound according to claim 1 wherein the hydroxy group attached to the carbon atom in position 15 is in α-configuration.

3. A compound according to claim 1 which is methyl 9-oxo-11α,15α-dihydroxy-16-phenoxy-17,18,19,20-tetranorprosta-trans-2-trans-13-dienoate and cyclodextrin clathrates thereof.

4. Pharmaceutical compositions which comprise, as active ingredient, a compound as claimed in claim 1 or a cyclodextrin clathrate thereof or when R in formula VI depicted in claim 1 represents a hydrogen atom, a non-toxic salt thereof, in association with a pharmaceutical carrier or coating.

5. A method for the stimulation of uterine contraction, or the production of an abortifacient, luteolytic or antinidatory effect, in female mammals which comprises the administration to the female mammal of a compound as claimed in claim 1 or a cyclodextrin clathrate thereof or, when R in formula VI depicted in claim 1 represents a hydrogen atom, a non-toxic salt thereof.

6. A method for the termination of pregnancy or the induction of labour in pregnant human females, the treatment of impaired fertility, the control of oestrus, contraception or menstrual regulation in human females, which comprises the oral, intravaginal, intrauterine, intravenous, intramuscular or extraovular administration to the human female of a dose of between 0.05 and 500 μg of a compound as claimed in claim 1 or a cyclodextrin clathrate thereof or, when R in formula VI depicted in claim 1 represents a hydrogen atom, a non-toxic salt thereof.

7. A method for the synchronisation of oestrus, treatment of impaired fertility or the termination of pregnancy or induction of labour in domestic female mammals which comprises the intramuscular, subcutaneous, intrauterine, intravaginal or intravenous administration of a dose per animal of between 0.01 and 50 mg of a compound as claimed in claim 1 or a cyclodextrin clathrate thereof or, when R in formula VI depicted in claim 1 represents a hydrogen atom, a non-toxic salt thereof.

8. A method for the inhibition of gastric acid secretion which comprises the administration of a compound as claimed in claim 1 or a cyclodextrin clathrate thereof or, when R in formula VI depicted in claim 1 represents a hydrogen atom, a non-toxic salt thereof.

9. A method for the treatment of gastric ulceration in the human adult which comprises the oral administration of a dose of between 20 and 500 μg of a compound as claimed in claim 1 or a cyclodextrin clathrate thereof or, when R in formula VI depicted in claim 1 represents a hydrogen atom, a non-toxic salt thereof.

10. A compound of the formula:

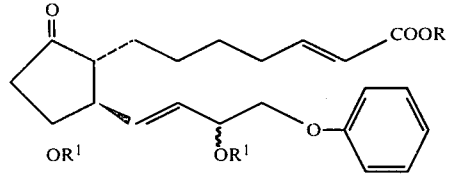

VII wherein R is as defined in claim 1, $R^1$ represents a 2-tetrahydrofuranyl or 1-ethoxyethyl group or a 2-tetrahydropyranyl group unsubstituted or substituted by at least one alkyl group and the depicted carbon-carbon double bonds are trans.

11. A compound according to claim 10 which is methyl 9-oxo-11α,15α-bis(2-tetrahydropyranyloxy)-16-phenoxy-17,18,19,20-tetranorprosta-trans-2,trans-13-dienoate.

* * * * *